United States Patent [19]

Yorozu et al.

[11] Patent Number: 5,217,719

[45] Date of Patent: Jun. 8, 1993

[54] SURFACE-TREATED SODIUM BICARBONATE PARTICLE AND MOLDED PREPARATION THEREOF

[75] Inventors: Hidenori Yorozu, Utsunomiya; Yuji Ichii, Ichikai; Kiyoshi Matsumoto; Masayuki Hashimoto, both of Utsunomiya; Masato Hoshi, Ujiie, all of Japan

[73] Assignee: Kao Corporation, Tokyo, Japan

[21] Appl. No.: 451,250

[22] Filed: Dec. 15, 1989

[30] Foreign Application Priority Data

Jan. 9, 1989 [JP] Japan .................................. 1-2569

[51] Int. Cl.$^5$ .............................................. A61K 9/46
[52] U.S. Cl. ......................................... 424/466; 424/490;
424/470; 424/469; 424/717; 423/422
[58] Field of Search ............... 423/422, 425; 252/192,
252/193, 183.16; 424/466, 469, 470, 717, 605,
490; 502/10

[56] References Cited

U.S. PATENT DOCUMENTS

| | | | |
|---|---|---|---|
| 261,228 | 7/1882 | Hemje et al. | 423/422 |
| 287,128 | 10/1883 | Hemje | 423/422 |
| 3,701,737 | 10/1972 | Goldstein | 423/425 |
| 3,852,427 | 12/1974 | Hoffman et al. | 423/422 |
| 3,855,398 | 12/1974 | Hoffmann et al. | 423/422 |
| 4,309,408 | 1/1982 | Pathak et al. | 514/619 |

OTHER PUBLICATIONS

Shreve, Norris R., Chemical Process Industries, 3rd Ed, 1967, pp. 228-231.

*Primary Examiner*—Michael Lewis
*Assistant Examiner*—Stuart L. Hendrickson
*Attorney, Agent, or Firm*—Oblon, Spivak, McClelland, Maier & Neustadt

[57] ABSTRACT

Surface-treated sodium bicarbonate particles, the surfaces of which are coated with sodium carbonate or its double salt, are disclosed. Heat treatment or irradiation with micro waves o infrared light converts the surfaces of sodium bicarbonate particles into sodium carbonate. The surface-treated sodium bicarbonate particles exhibit an increased capacity to bind with other sodium bicarbonate particles as well as with other components when they are molded. They can be used as an excellent binder for molding various preparations. The products produced have a prolonged storage stability.

4 Claims, 4 Drawing Sheets

SURFACE-TREATED SODIUM BICARBONATE PARTICLE AND MOLDED PREPARATION THEREOF

BACKGROUND OF THE INVENTION

1. Field of the Invention

The present invention relates to surface-treated sodium bicarbonate particles, and, more particularly, to surface-treated sodium bicarbonate particles exhibiting an increased capacity to bind with other sodium bicarbonate particles as well as with other components when they are molded. The invention also relates to molded preparations comprising such surface-treated sodium bicarbonate particles.

2. Description of the Background

Sodium bicarbonate is very frequently molded into tablets, granules, or the like for use as effervescent tablets of bathing agents, digesting agents, gargles, vaginal agents, etc. Sodium bicarbonate particles, however, possess only a poor capacity to bind with other sodium bicarbonate particles or with other components, resulting in difficulties in molding operations, especially in high-speed molding operations. For this reason, the use of a considerable amount of binder has been imperative for molding compositions containing sodium bicarbonate particles. The use of a large amount of binder, however, inevitably results in a decrease in the sodium bicarbonate amount in a molded product. This necessitates the administration of a large amount of a drug to the user, thus producing them a disagreeable feeling. Production costs also increase as a result of the use of such a large amount of binder.

Although various studies directed t the development of binders exhibiting a higher binding effect have been undertaken, none of these studies have so far been successful.

In view of this situation, the present inventors have undertaken extensive studies, and, as a result, have found that the binding capacity of sodium bicarbonate particles could remarkably be improved by coating their surfaces with sodium carbonate or its double salt. Such a finding has led to the completion of the present invention.

SUMMARY OF THE INVENTION

Accordingly, an object of the present invention is to provide surface-treated sodium bicarbonate particles, the surfaces of which are coated with sodium carbonate or its double salt.

In a preferred embodiment of the present invention, the surface-treated sodium bicarbonate particles have 5 kg or more of binding power.

Another object of the present invention is to provide a binder comprising such surface-treated sodium bicarbonate particles.

Still another object is to provide molded preparations comprising such surface-treated sodium bicarbonate particles.

Other objects, features and advantages of the invention will hereinafter become more readily apparent from the following description.

DETAILED DESCRIPTION OF THE INVENTION AND PREFERRED EMBODIMENTS

Figure 1:
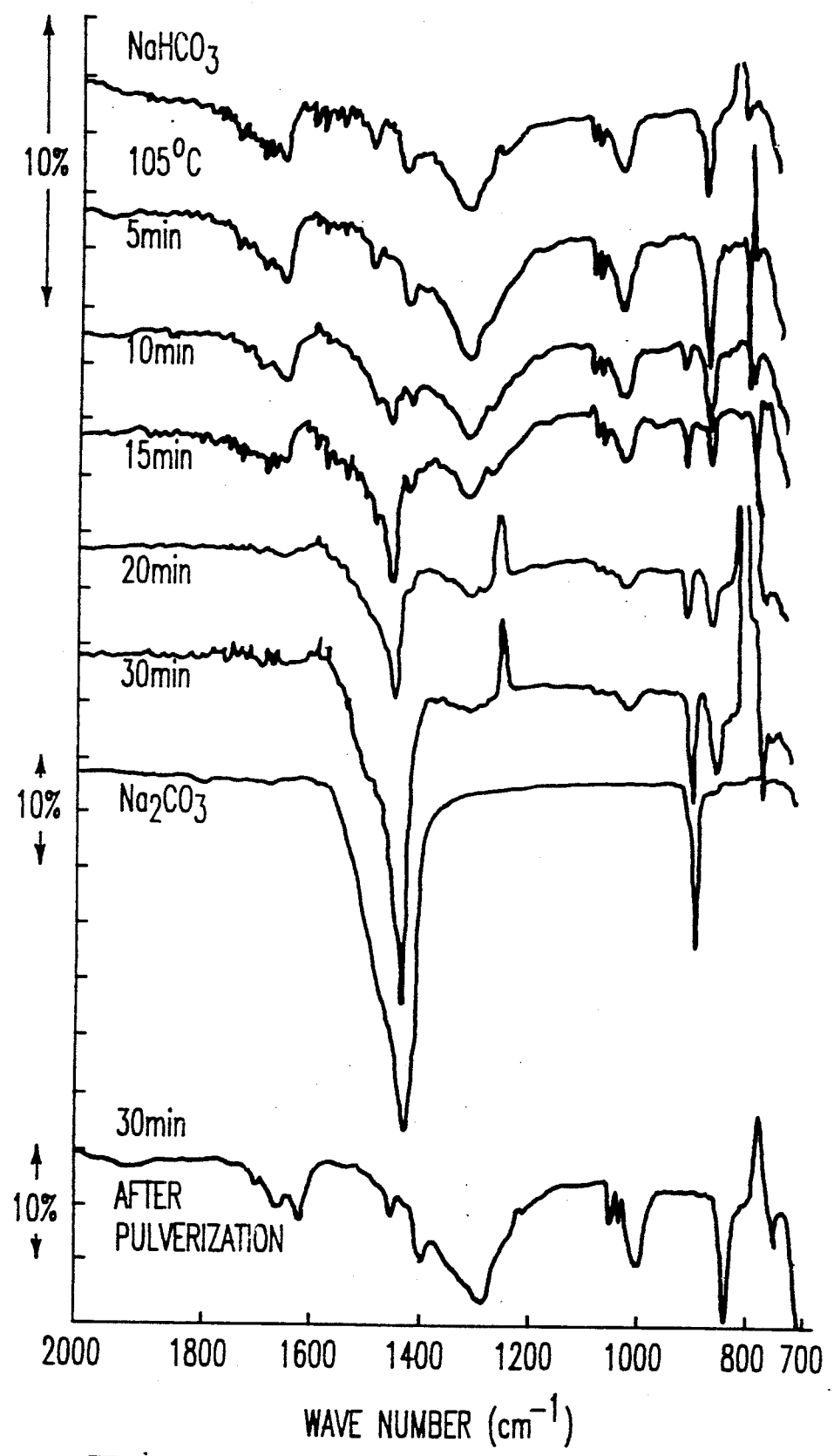
FIG. 1 shows ATR (attenuated total reflection) IR spectra over time when sodium bicarbonate was heated.

Although there are no specific restrictions as to the average particle size of the sodium bicarbonate particles of the present invention, a size greater than 30 $\mu$m is preferable. It is desirable that the whole surface of the sodium bicarbonate particles of the present invention be covered with sodium carbonate or its double salt. A satisfactory result can, however, be obtained when 50 percent or more of the surfaces are covered by sodium carbonate or its double salt. It is imperative that at least a part of the sodium bicarbonate particles be covered by sodium carbonate. The effect of the present invention, however, cannot be obtained by merely mixing sodium bicarbonate and sodium carbonate. A preferable thickness of the sodium carbonate layer which covers sodium bicarbonate particle surfaces is from 0.1 $\mu$m to a thickness equivalent to 20% of the particle size of sodium bicarbonate, with a particularly preferable range being 0.1–5 $\mu$m.

The following methods (1)–(4) are given as examples of a method for covering surfaces of sodium bicarbonate particles with sodium carbonate.

(1) Heat sodium bicarbonate particles to a temperature above 70° C. Sodium bicarbonate particles having an average diameter of 200 $\mu$m, for example, can be converted into sodium carbonate for a depth of approximately 1 $\mu$m from the surface when heated to about 100° C. for 30 minutes. The thickness of sodium carbonate on the surface can be controlled by the heating temperature and the heating time.

(2) Heat sodium bicarbonate particles under reduced pressure at a temperature below 70° C. Sodium bicarbonate particles, for example, are heated at a temperature below 70° C. and 10 mmHg for 120 minutes.

(3) Cause sodium bicarbonate particles to come into contact with an inert gas. Sodium bicarbonate particles are heated in an inert gas at the same temperature and for the same period of time as in (1) above.

(4) Irradiate sodium bicarbonate particles with micro waves or infrared light.

In a preferred embodiment of the present invention, sodium bicarbonate particles have 5 kg or more of binding power, when measured by a method described in Example 2 hereinafter.

Sodium bicarbonate particles of the present invention thus produced have a strong binding capacity and can therefore be molded into tablets or granules without using a binder. Given as examples of molded preparations which are made from sodium bicarbonate particles of the present invention are foaming preparations molded in conjunction with an acid such as bathing agent tablets, soft drink tablets, and the like, and effervescent tablets of digesting agents, gargles, vaginal agents, and the like which are prepared by using the sodium bicarbonate particles independently or in combination with other pharmaceutical components. In particular, forming preparations in which the sodium bicarbonate particles of the present invention are used in combination with an acid not only have an improved molding capability but also exhibit a superior stability during storage at a higher temperature. Such preparations are thus suitable for products requiring a prolonged storage time. A specific example of a molded bathing preparation is a weakly acidic one which is prepared by molding a mixture of the surface-treated sodium bicarbonate particles of the present invention and a water-soluble solid acid such as succinic acid, adipic acid, fumaric acid, phosphoric acid, or the like. An amount of an acid to be formulated into such a bathing preparation should be such that the bath water to which the preparation is added, normally at a concentration of about 0.01%, for example, becomes weakly acidic, i.e., pH 4–7, and preferably pH 6.0–6.7.

Besides acidic bathing preparations, the surface-treated sodium bicarbonate particles of the present invention can be used as an excellent binder for molding various preparations because of their superior binding power. They can be molded alone without using a binder or can be used as a binder together with other components for producing tablets, granules, and the like. The molded preparations using the surface-treated sodium bicarbonate particles of this invention have a superior storage stability.

Other features of the invention will become apparent in the course of the following description of the exemplary embodiments which are given for illustration of the invention and are not intended to be limiting thereof.

EXAMPLES

Example 1

Figure 2:
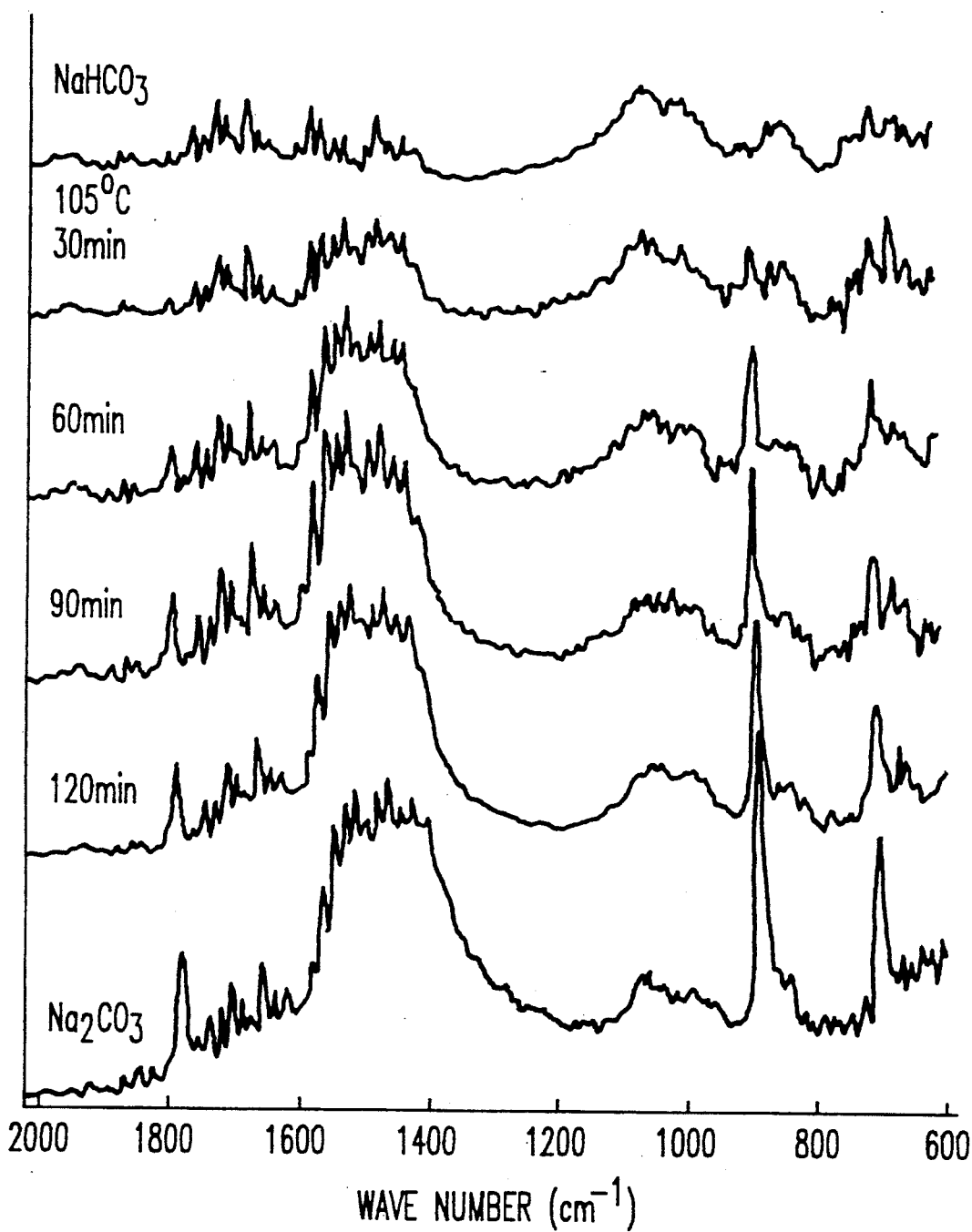
FIG. 2 shows PAS (photoacoustic spectroscopy) IR spectra over time when sodium bicarbonate was heated.
Figure 3:
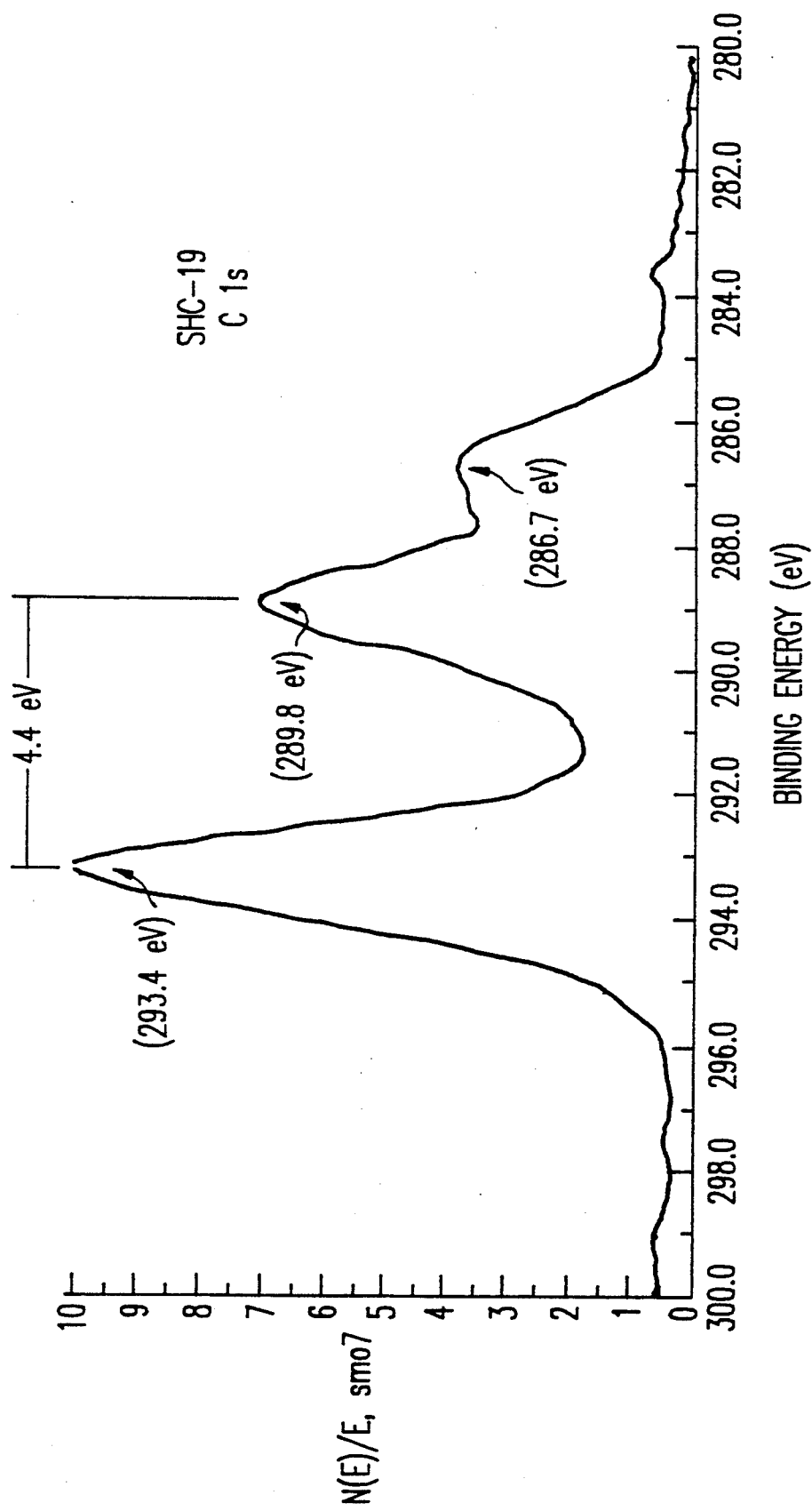
FIG. 3 shows an XPS (x-ray photoemission spectroscopy) spectrum when sodium bicarbonate was heated at 105° C. for 10 minutes

Sodium bicarbonate having an average particle diameter of 200 $\mu$m (manufactured by Toyo Soda Manufacturing Co., Ltd.) was heated to 105° C. In order to observe the changes in sodium bicarbonate particles over time IR spectra with different analytical depths (ATR method and PAS method) and by the X ray photoelectron spectrum (XPS) method were measured. The results are shown in FIGS. 1–3.

As is evidenced by the ATR spectra of FIG. 1, heating for a period of 20–30 minutes converted the sodium bicarbonate particle surface of about 1 $\mu$m thickness into sodium carbonate. The spectrum obtained from a pulverized sample which was heated for 30 minutes was almost identical with the spectrum of sodium bicarbonate, showing that the structure of bulk sodium bicarbonate and that of the particle surface are different. As demonstrated by the PAS spectrum of FIG. 2, heating for 90–120 minutes converted 10-$\mu$m-thick sodium bicarbonate on the particle surface into sodium carbonate. At a 50–100 Angstrom polar surface, all of the sodium bicarbonate changed into sodium carbonate by heating for 10 minutes as can be seen from the XPS spectrum of FIG. 3. These results confirm that sodium bicarbonate particles with their surfaces covered with sodium carbonate can be produced by heating.

Example 2

The binding powers were measured on sodium bicarbonate samples (average particle diameter: 200 $\mu$m; manufactured by Toyo Soda Manufacturing Co., Ltd.) which were subjected to the treatments listed in Table 1. Fifteen (15) g of a sample was placed into a pestle having a 30-mm diameter. A pressure of 200 kg was applied by means of an oil pressure tableting machine (manufactured by Riken Co., Ltd.) to produce tablets (n=3). The hardness (kg) of the tablets produced was measured by a Kiya Hardness Meter (No. 1600-C: trade name) having a sample supporting table with a diameter of 50 mm and at the pressurized diameter of 5 mm. The resulting value of the hardness was taken as the binding power of the sample. The results are shown in Table 1.

TABLE 1

| Sample No. | Treating Conditions | Hardness (kg/unit surface area) |
| --- | --- | --- |
| 1 | Untreated sodium bicarbonate | 3.6 |
| 2 | Sodium bicarbonate heated at 105° C. for 10 minutes. | 7.1 |
| 3 | Sodium bicarbonate heated at 105° C. for 30 minutes. | 11.0 |
| 4 | Sodium bicarbonate heated at 105° C. for 90 minutes. | 14.3 |
| 5 | A mixture of sodium bicarbonate/sodium carbonate (9/1) | 2.3 |
| 6 | A mixture of sodium bicarbonate/sodium carbonate (8/2) | 3.3 |
| 7 | A mixture of sodium bicarbonate/sodium carbonate (7/3) | 3.7 |

The results in Table 1 indicate that the surface-treated sodium bicarbonate particles of the present invention had remarkably improved binding powers as compared with untreated sodium bicarbonate particles. Merely mixing sodium bicarbonate and sodium carbonate did not improve the binding power.

Example 3

Figure 4:
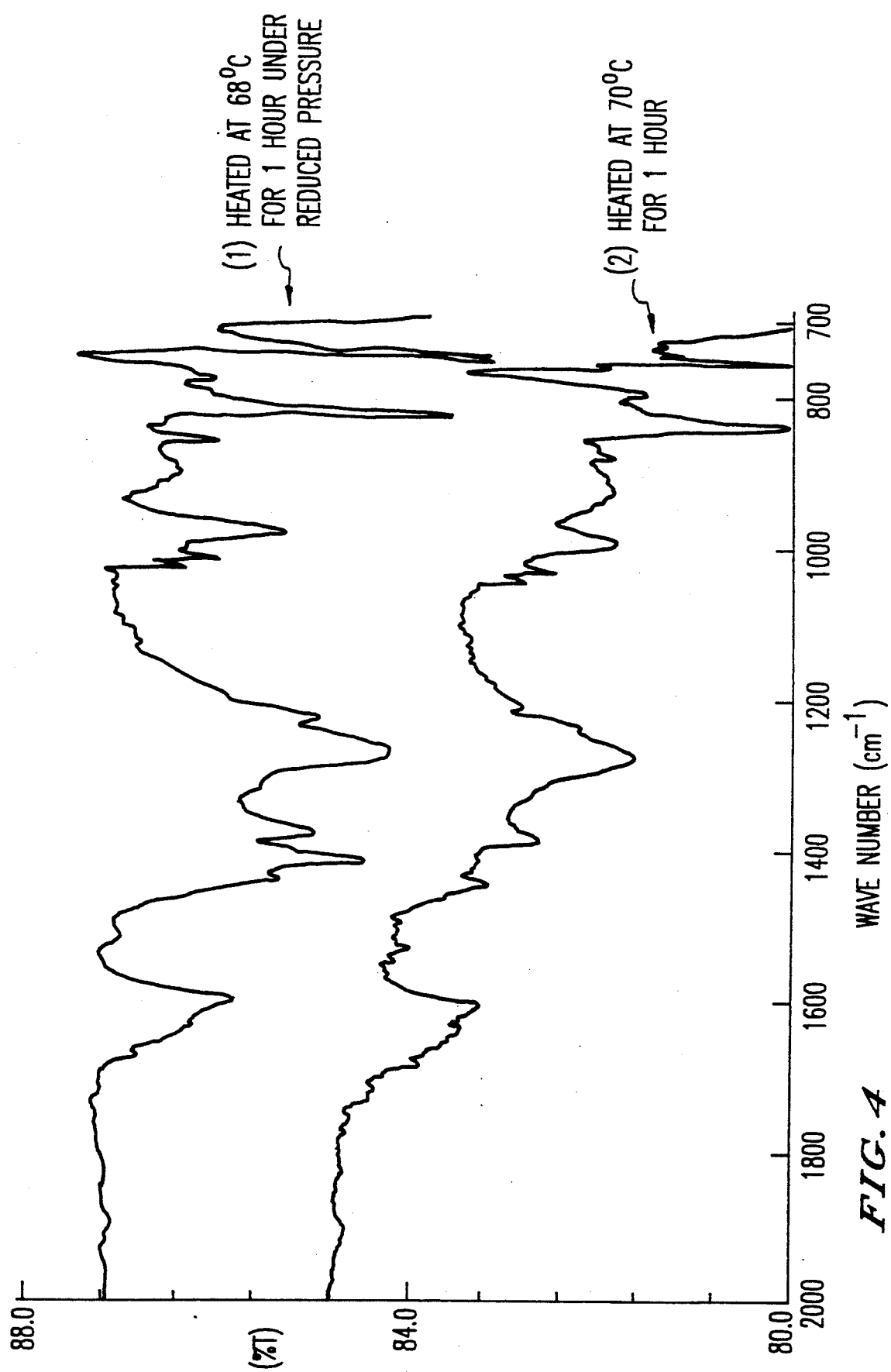
FIG. 4 shows ATR (attenuated total reflection) IR spectra of the sample used in Example 3 hereinafter.

Two lots of sample sodium bicarbonate having an average particle diameter of 200 $\mu$m (manufactured by Toyo Soda Manufacturing Co., Ltd.) were provided for the test. One was heated at 68° C. under reduced pressure (10 mmHg) for 1 hour and the other was heated at 70° C. under atmospheric pressure for 1 hour. An ATR spectrum was measured on each treated sample. The results are shown in FIG. 4, which indicate that the second sample, which was treated under atmospheric pressure, was almost the same as the untreated sample, while the reaction proceeded considerably in the first sample which was heated under reduced pressure. This first sample, was pulverized and the ATR spectrum of the powdered sample was measured. The spectrum was almost the same as that of sodium bicarbonate. This confirms that the surfaces of the sodium bicarbonate particles were covered with sodium carbonate.

The binding powers of the two treated samples were measured in the same way as in Example 2. The first sample had a 10.7 kg hardness, while the hardness of the second sample was 3.3 kg, demonstrating a remarkable improvement in the binding power of the sodium bicarbonate particles treated under reduced pressure over those treated under atmospheric pressure.

Example 4

Bathing agents were prepared from 500 kg of succinic acid, 350 kg of sodium bicarbonate (untreated or surface-treated, No. 4 sample product of Example 2), 100 kg of sodium carbonate, 45 kg of polyethylene glycol, 3 kg of dextrin, 1.5 kg of a perfume, and 0.5 kg of a coloring agent (total weight: 1,000 kg). These components were blended, screened through a 16 mesh sieve to remove large particles, and tableted using a tableting machine (DC-WD type, manufactured by Machina Co., Ltd.) to produce bathing agent tablets weighing 50 g each. The tablets were packed with aluminum foils laminated with a polymer membrane. The packages were heat-sealed.

The bathing agent products were evaluated for their binding power, occurrence of capping, and stability according to the following methods.

Binding power: 15 g of a sample was placed into a pestle having a 30 mm diameter. A pressure of 200 kg was applied by means of an oil pressure tableting machine to produce tablets. The hardness (kg) of the produced tablets was measured by a Kiya Hardness Meter.

Capping occurrence: Tablets were continuously produced using a tableting machine (DC-WD type, manufactured by Machina Co., Ltd.) with varied tableting speeds to determine the minimum speed at which capping occurred.

Stability: Ten (10) packages were left in a thermostat at a temperature of 50° C. for 24 hours. The volume changes before and after the packages were treated were determined. The average values were calculated from the results. The lower the value, the more stable the tablet.

The results are shown in Table 2.

TABLE 2

| Sample | Binding power (kg) | Capping occurrence | Stability (cc) |
|---|---|---|---|
| A: Bathing agent produced from surface-treated sodium bicarbonate | 6.9 | No problem at 25 tablets/min. | 0.2 |
| B: Bathing agent produced from untreated sodium bicarbonate | 4.4 | Capping occurred at above 22 tablets/min. | 3.4 |

As can be seen from Table 2, the bathing agent tablet using surface-treated sodium bicarbonate had improved binding power, did not result in a capping problem, and exhibited excellent stability.

Example 5

Bathing agents were prepared from 350 kg of succinic acid, 150 kg of fumaric acid, 350 kg of sodium bicarbonate (untreated or surface-treated; product of Toyo Soda Manufacturing Co., Ltd.; average particle diameter: 100 μm), 100 kg of sodium carbonate, 45 kg of polyethylene glycol, 3 kg of dextrin, 1.5 kg of a perfume, and 0.5 kg of a coloring agent (total weight: 1,000 kg). These components were blended, screened through a 16 mesh sieve to remove large particles, and tableted using a tableting machine (DC-WD type, manufactured by Machina Co., Ltd.) to produce bathing agent tablets weighing 50 g each. The tablets were packed with aluminum foils laminated with a polymer membrane. The packages were heat-sealed.

The bathing agent products were evaluated for their binding power according to the method described in Example 4. The results are shown in Table 3.

Example 6

Bathing agents were prepared from 350 kg of succinic acid, 100 kg of fumaric acid, 550 kg of sodium bicarbonate (untreated or surface-treated; product of Toyo Soda Manufacturing Co., Ltd.; average particle diameter: 100 μm), 45 kg of polyethylene glycol, 3 kg of dextrin, 1.5 kg of a perfume, and 0.5 kg of a coloring agent (total weight: 1,500 kg). These components were blended, screened through a 16 mesh sieve to remove large particles, and tableted using a tableting machine (DC-WD type, manufactured by Machina Co., Ltd.) to produce bathing agent tablets weighing 50 g each. The tablets were packed with aluminum foils laminated with a polymer membrane. The packages were heat-sealed.

The bathing agent products were evaluated for their binding power according to the method described in Example 4. The results are shown in Table 3.

TABLE 3

| Sample | Binding power (kg) |
|---|---|
| C: Bathing agent produced from surface-treated sodium bicarbonate (Example 5) | 12.9 |
| D: Bathing agent produced from untreated sodium bicarbonate | 7.1 |
| E: Bathing agent produced from surface-treated sodium bicarbonate (Example 6) | 6.5 |
| F: Bathing agent produced from untreated sodium bicarbonate | 3.8 |

Example 7

Sodium bicarbonate (average particle diameter: 100 μm, manufactured by Asahi Glass Co., Ltd.) was heat-treated at 120° C. for 10 minutes. Thirty three (33) kg of this surface-treated sodium bicarbonate, 49.4 kg of synthetic aluminum silicate, 16 kg of magnesium oxide, 0.6 kg of turkey red oil extract, and 1 kg of magnesium oxide (total weight: 100 kg) were blended and tableted using an eccentric type tableting machine (manufactured by Kikusui Manufacturing Co., Ltd.) to produce bathing agent tablets weighing 30 g each.

Obviously, numerous modifications and variations of the present invention are possible in light of the above teachings. It is therefore to be understood that within the scope of the appended claims, the invention may be practiced otherwise than as specifically described herein.

What is claimed is:

1. A molded preparation comprising: surface-treated sodium bicarbonate particles having a core of sodium bicarbonate that is at least partially coated with a thickness of 0.1 μm to 20% of the particle size with sodium carbonate or a double salt of sodium carbonate wherein said surface-treated particles are distributed throughout said molded preparation.

2. A molded preparation according to claim 1, wherein said surface-treated sodium bicarbonate particles have 5 kg/unit surface area or more of binding power.

3. A molded preparation comprising surface-treated sodium bicarbonate particles having a core of sodium bicarbonate that is at least partially coated with a thickness of 0.1 μm to 20% of the particle size with sodium carbonate or a double salt of sodium carbonate; and a water-soluble solid acid selected from the group consisting of succinic acid, adipic acid, fumaric acid and phosphoric acid wherein said surface-treated sodium bicarbonate particles are distributed throughout said molded preparation.

4. A molded preparation according to claim 3, wherein said surface-treated sodium bicarbonate particles have 5 kg/unit surface area or more of binding power.

* * * * *